United States Patent [19]

Kaneko

[11] Patent Number: 5,555,040
[45] Date of Patent: Sep. 10, 1996

[54] OPHTHALMIC ILLUMINATION APPARATUS HAVING A DEVICE THAT SHADES ILLUMINATING LIGHT

[75] Inventor: Masanobu Kaneko, Yokohama, Japan

[73] Assignee: Nikon Corporation, Tokyo, Japan

[21] Appl. No.: 489,376

[22] Filed: Jun. 12, 1995

[30] Foreign Application Priority Data

Jun. 17, 1994 [JP] Japan .................................. 6-159575

[51] Int. Cl.$^6$ .................................................. A61B 3/10
[52] U.S. Cl. .................................................. 351/221
[58] Field of Search .................................. 351/200, 205, 351/213, 214, 221; 359/40, 245, 265

[56] References Cited

U.S. PATENT DOCUMENTS 5,436,679  7/1995  Ohtsuka et al. ............... 351/221 X

FOREIGN PATENT DOCUMENTS 60-111625  6/1985  Japan .

*Primary Examiner*—William L. Sikes
*Assistant Examiner*—Huy Mai
*Attorney, Agent, or Firm*—Shapiro and Shapiro

[57] ABSTRACT

An ophthalmic illumination apparatus for illuminating an eye to be examined with light comprises a light source emitting illuminating light, shading means including an electrical light control element of which the transmittance is electrically varied and shading at least part of the illuminating light, and control means for electrically varying the transmittance of the shading means.

8 Claims, 4 Drawing Sheets

OPHTHALMIC ILLUMINATION APPARATUS HAVING A DEVICE THAT SHADES ILLUMINATING LIGHT

BACKGROUND OF THE INVENTION

1. Field of the Invention

This invention relates to an ophthalmic illumination apparatus, and particularly to improvements in the illuminating optical system of a microscope for operation, and more particularly to an apparatus for protecting the tissue of the fundus of an eye from excessive illuminating light.

2. Related Background Art

In recent years, operations for cataracts have been widely performed and microscopes for operation are requisite during operation. However, the illuminating light of microscopes for operation is very great in its intensity and the time for operation is relatively long and therefore, the tissue of the fundus of an eye may be injured by rays of light which have entered from the pupil of an eye to be examined.

For this reason, various propositions have heretofore been made to protect the tissue of an eye from the excessive illuminating light of a microscope for operation.

For example, Japanese Patent Application Laid-open No. 60-111625 discloses a technique of disposing a light absorbing layer in a plane in the central area of an illuminating optical path which is conjugate with an object surface, and inserting the light absorbing layer into an illuminating optical system as required.

In the above-described apparatus according to the prior art, however, the illuminating light is all shaded by the light absorbing layer. This has led to the inconvenience that even when more or less brightness is necessary in a portion to be treated as in the suturing treatment during an operation, the portion to be treated becomes too dark due to the light absorbing layer and the operation becomes difficult.

Also, the light absorbing layer which is a shading member, must be mechanically mounted and dismounted. This has led to the inconvenience that each time the shading operation is performed, vibration is created, and as a result, the vibration is also transmitted to the microscope.

Further, the shape of the light absorbing layer cannot be changed. This has led to the inconvenience that the apparatus cannot cope with any variation in the size of the pupil of an eye to be examined.

SUMMARY OF THE INVENTION

The present invention has been made in view of the above-noted problems and the object thereof is to provide an ophthalmic illumination apparatus in which the transmittance and shape of a shading portion can be suitably varied and moreover no vibration is created with the shading operation.

In order to solve the above-noted problems, the present invention provides an ophthalmic illumination apparatus for illuminating an eye to be examined with light, characterized by the provision of shading means for shading illuminating light including an electrical light control element of which the transmittance is electrically varied, and control means for electrically varying the transmittance of said shading means.

According to a preferred embodiment of the present invention, said shading means is provided at a position substantially conjugate with the pupil of the eye to be examined. Also, said control means may preferably reduce the transmittance of said shading means continuously or stepwisely on the basis of the intensity of the illuminating light as, for example, the intensity of the illuminating light increases.

In the ophthalmic illumination apparatus of the present invention, the illuminating light is shaded by the use of the electrical light control element of which the transmittance is electrically varied. That is, by the transmittance being suitably varied, the eye to be examined can be illuminated with such suitable brightness that the tissue of the fundus of the eye to be examined is not injured.

Also, the shading operation is performed by an electrical variation in the transmittance and therefore, unlike the mounting and dismounting of a mechanical shading member, no vibration is created during the shading operation. Accordingly, no vibration is transmitted to a microscope for operation and thus, the eye to be examined becomes easy to observe.

DESCRIPTION OF THE PREFERRED EMBODIMENTS

Some preferred embodiments of the present invention will hereinafter be described with reference to the accompanying drawings.

Figure 1:
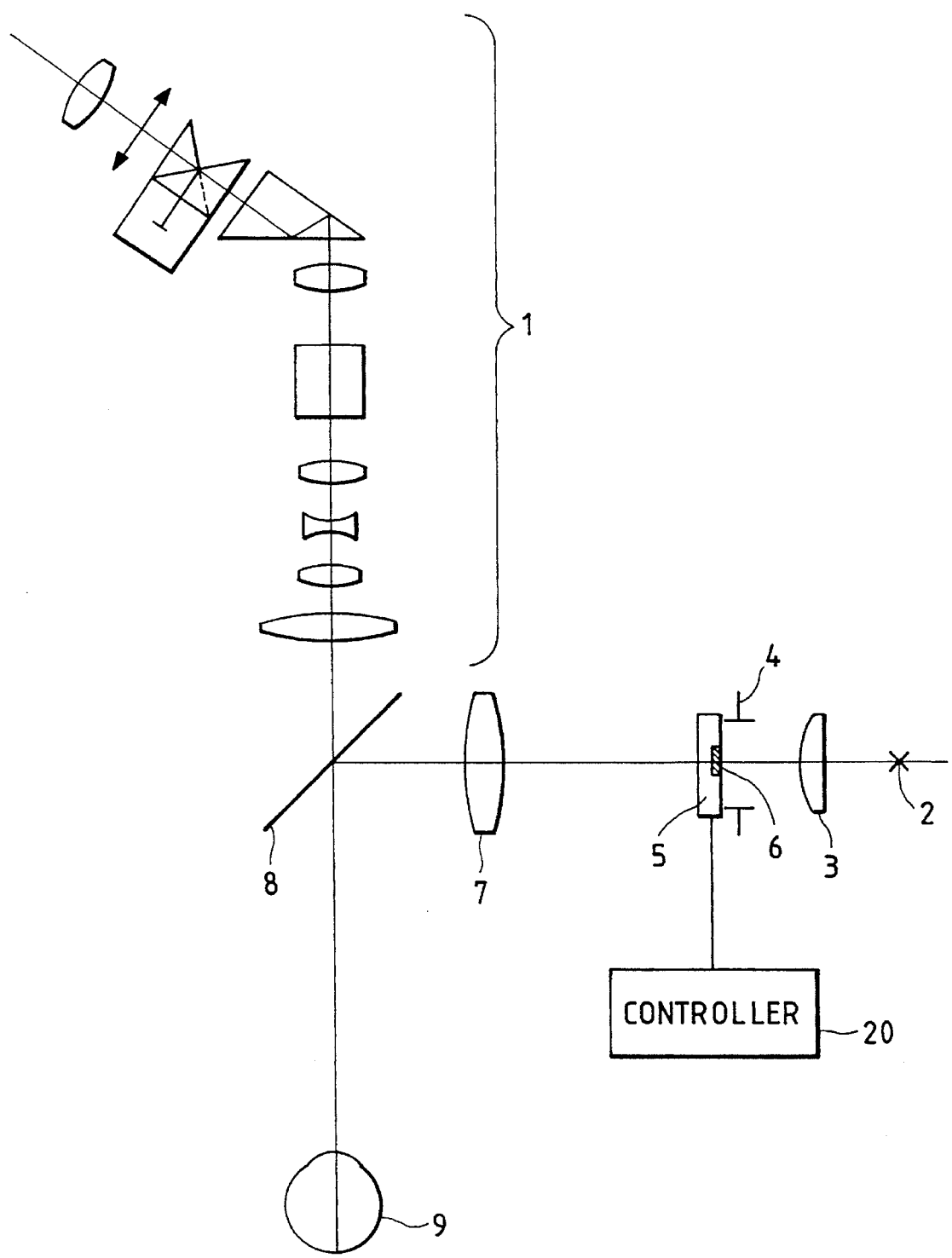
FIG. 1 shows the construction of an ophthalmic illumination apparatus according to a first embodiment of the present invention with a microscope optical system.

FIG. 1 shows the construction of an ophthalmic illumination apparatus according to a first embodiment of the present invention with a microscope optical system. In FIG. 1, the reference numeral 1 designates the microscope optical system.

The ophthalmic illumination apparatus shown is provided with an illuminating light source 2. Illuminating light emitted from the illuminating light source 2 is condensed by a condenser lens 3 and illuminates an illumination field stop 4. In an illuminating optical system which is not provided with a shading member, nothing is provided near the illumination field stop 4 and therefore, the illuminating light passed through the illumination field stop 4 passes through a relay lens 7 for illumination, whereafter it is reflected downwardly by light dividing means 8 as viewed in FIG. 1 and illuminates the eye 9 to be examined.

Since the field stop 4 is substantially conjugate with the pupil of the eye 9 to be examined, the eye 9 to be examined is illuminated in the shape (usually circular shape) of the illumination field stop 4.

Figure 2:
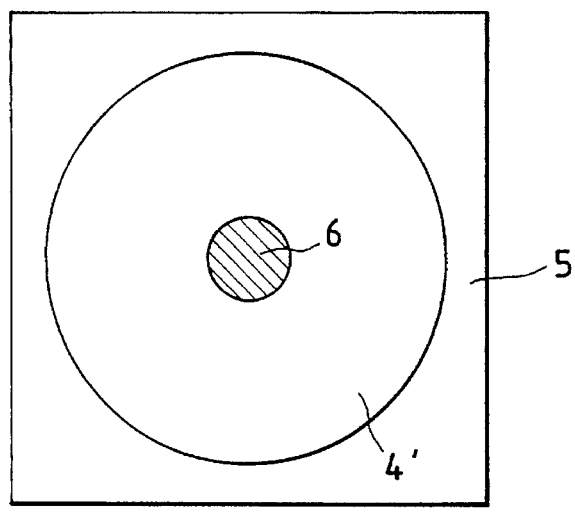
FIG. 2 shows the construction of the shading member 5 of FIG. 1 along a plane perpendicular to an optical axis.

In the apparatus of the present embodiment, a shading member 5 is provided at or near the location of the illumination field stop 4. FIG. 2 shows the construction of the shading member 5 of FIG. 1 along a plane perpendicular to the optical axis thereof. As shown in FIG. 2, the shading member 5 has a shading portion 6 within a range 4' corresponding to the illumination field stop 4. Accordingly, the image of the shading portion 6 of the shading member 5 is also formed near the pupil of the eye 9 to be examined. The shading portion 6 comprises an electrical light control element (herein a whole solid state type electrochromic element) of which the transmittance can be electrically varied. The transmittance of the electric light control element is electrically controlled by a controller 20.

In an operation for a cataract, it is necessary to illuminate the front eye part of the eye 9 to be examined brightly until an intraocular lens is inserted into the eye 9 to be examined. Accordingly, until the stage at which the intraocular lens is inserted, the shading portion 6 of the shading member 5 is transparent and the illuminating light illuminates the eye 9 to be examined with sufficient brightness without being shaded by the shading member 5.

At the stage of suturing treatment thereafter, it is desirable to illuminate the eye to be examined within such a range that the tissue of the fundus of the eye is not injured, while securing such a degree of brightness which will not hinder the suturing treatment. Accordingly, at the stage of suturing treatment, the transmittance of the shading portion 6 comprising an electrical light control element is suitably reduced and the illuminating light is shaded to a certain degree. As a result, the eye 9 to be examined can be illuminated with such a degree of brightness that is sufficient for the suturing treatment and does not injure the tissue of the fundus of the eye.

The operation of varying the transmittance of the shading portion 6 is electrically performed through control means, not shown. Therefore, unlike the prior-art method wherein shading is effected by the operation of mechanically mounting and dismounting the shading means, no vibration is created by the shading operation. Accordingly, the microscope optical system is not subjected to vibration and the eye to be examined can be observed well through the microscope optical system.

When, by an operator's intention, the intensity of the illuminating light is changed depending on the convenience of the eye 9 to be examined, the illuminating light may become too dark or too bright. For example, when the intensity of the illuminating light is made relatively small and the eye 9 to be examined is illuminated, if the transmittance of the shading portion 6 is low, the illuminating light will be shaded too much and the central portion of the eye 9 to be examined will become too dark.

When, conversely, the intensity of the illuminating light is made relatively great and the eye 9 to be examined is illuminated, if the transmittance of the shading portion 6 is low, the central portion of the eye 9 to be examined will be illuminated too brightly.

Figure 3:
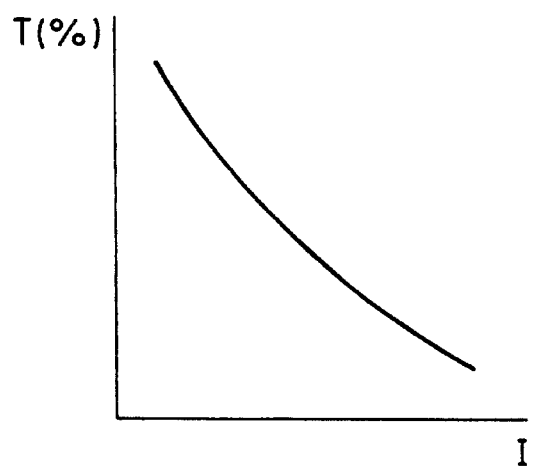
FIG. 3 is a graph showing the relation between the transmittance T(%) of the shading portion of the shading member 5 of FIG. 1 and the intensity I of illuminating light.
Figure 4:
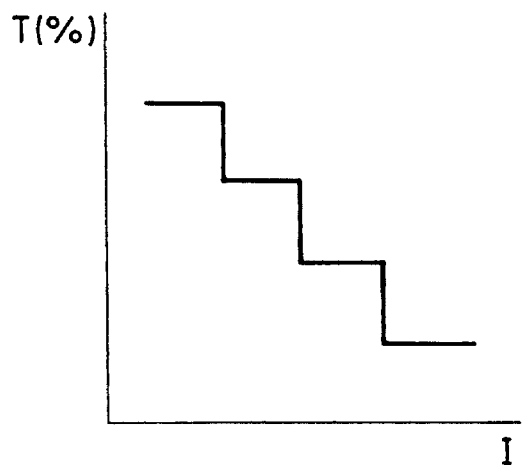
FIG. 4 is a graph showing the relation between the transmittance T(%) of the shading portion of the shading member 5 of FIG. 1 and the intensity I of illuminating light.

In order to avoid such an inconvenience in the apparatus of the present embodiment, by utilizing the fact that the transmittance T(%) of the electrical light control element which is the shading portion 6 of the shading member can be freely controlled, the transmittance T(%) varies continuously or stepwisely as shown in FIG. 3 or 4 as the intensity I of the illuminating light becomes greater.

Accordingly, in the apparatus of the present embodiment, it does not happen that when the intensity of the illuminating light is made relatively small and the eye 9 to be examined is illuminated, the central portion of the eye 9 to be examined becomes too dark, or when the intensity of the illuminating light is made relatively great and the eye 9 to be examined is illuminated, the central portion of the eye 9 to be examined is illuminated too brightly.

Figure 5:
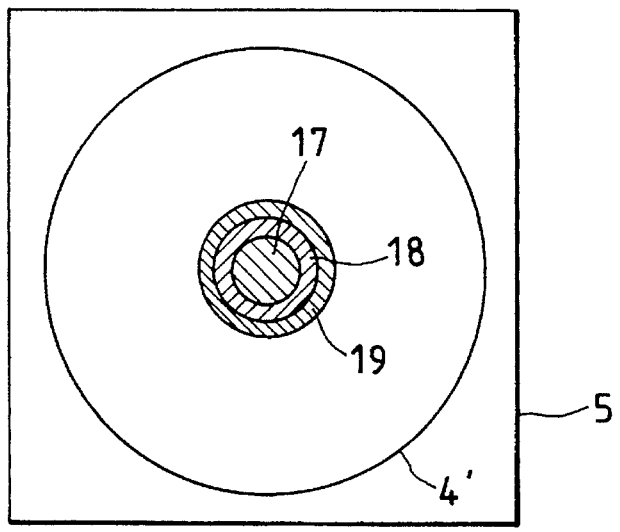
FIG. 5 shows the construction of the shading member of an ophthalmic illumination apparatus according to a second embodiment of the present invention.

FIG. 5 shows the construction of the shading member of an ophthalmic illumination apparatus according to a second embodiment of the present invention. The second embodiment is similar in construction to the first embodiment except for the shading member.

In the shading member 5 of the second embodiment, as shown in FIG. 5, the shading portion thereof is comprised of a circular shading portion 17 for shading the central portion, a ring-like shading portion 18 for shading a portion outside thereof, and a ring-like shading portion 19 for shading a portion further outside thereof.

The shading portions 17, 18 and 19 each are an electrical light control element of which the transmittance can be electrically varied. Accordingly, the sizes (i.e., the shapes) of the shading portions can be freely chosen in conformity with the size of the pupil of the eye to be examined. That is, when the pupil of the eye to be examined is small, only the transmittance of the shading portion 17 is reduced and the shading portions are made small, whereby that portion which became dark in the prior art in spite of needing not to be shaded can be illuminated brightly. When conversely, the pupil of the eye to be examined is large, the transmittances of the shading portions 17, 18 and 19 are reduced and the shading portions are made large, whereby that portion of the pupil which could not be shaded by the prior art can be shaded.

Figure 6:
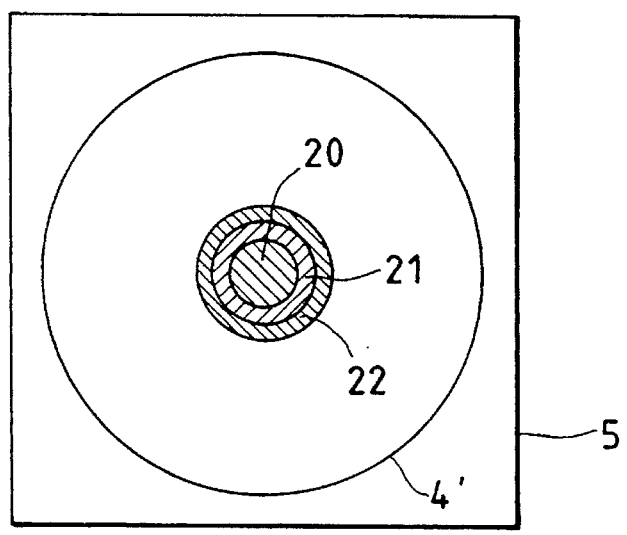
FIG. 6 shows the construction of the shading member of an ophthalmic illumination apparatus according to a third embodiment of the present invention.

FIG. 6 shows the construction of the shading member of an ophthalmic illumination apparatus according to a third embodiment of the present invention. The third embodiment is similar in construction to the first embodiment except for the shading member.

In the shading member 5 of the third embodiment, as in that of second embodiment, the shading portion thereof is comprised of a circular shading portion 20 for shading a portion central portion, a ring-like shading portion 21 for shading a portion outside thereof, and a ring-like shading portion 22 for shading the further outside thereof.

The shading portions 20, 21 and 22 each are an electrical light control element of which the transmittance can be electrically varied. However, this embodiment basically differs from the second embodiment in that the transmittance is lowest in the shading portion 20 and becomes increasingly higher, in order, in the shading portions 21 and 22. Thus, in the shading portion of the third embodiment, there is obtained a shading area having such a distribution of brightness that the transmittance increases from the central portion toward the marginal portion, that is, brightness gradually becomes higher from the central portion toward the marginal portion.

By such a shading distribution being obtained, the portion around the pupil of the eye to be examined can be illuminated brightly during suturing and also, even when positional deviation occurs between the illuminating light and the eye to be examined, the bright illuminating light can be prevented from suddenly entering the eye to be examined.

Figure 7:
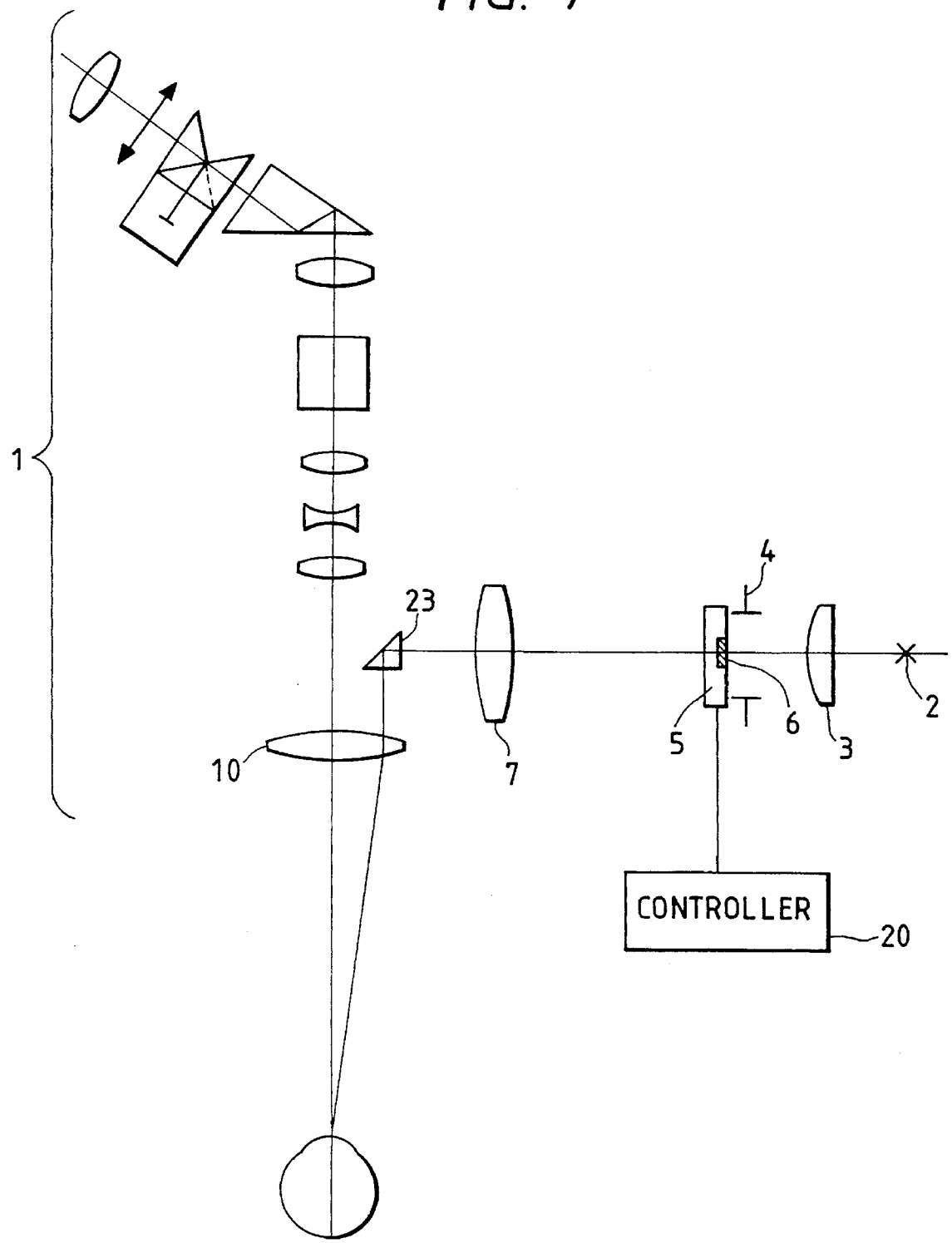
FIG. 7 shows the construction of an ophthalmic illumination apparatus according to a fourth embodiment of the present invention with a microscope optical system.

FIG. 7 shows the construction of an ophthalmic illumination apparatus according to a fourth embodiment of the present invention with a microscope optical system. The apparatus of the fourth embodiment is similar in construction to the apparatus of the first embodiment, but basically differs from the apparatus of the first embodiment in that a prism 23 is introduced instead of the light dividing means 8 in the first embodiment and the illuminating light deflected by the prism 23 is caused to enter the eye to be examined through the objective lens 10 of the microscope optical system 1.

In the other points of construction and operation, the fourth embodiment is similar to the first embodiment.

The electrical light control element may desirably be an electrochromic element of the whole solid state type, from the viewpoints of the magnitude of the variation in the transmittance thereof, the simplicity of the handling thereof, etc.

Also, regarding the injury by light to the fundus of the eye to be examined, it has been pointed out that light of a short wavelength is more dangerous than light of a long wavelength. Accordingly, it is desirable that the shading portion be an electrical light control element of such structure that will reduce the transmittance more for rays of a short wavelength.

Further, it is preferable that the shading member be removably constructed, so that it can be removed from the illuminating optical path when it is not needed.

While in the above-described embodiments, the present invention has been described with the illumination apparatus of a microscope for operation taken as an example, it is apparent that the present invention can be applied to an ordinary ophthalmic illumination apparatus.

Also, in the second and third embodiments, the shading portion comprises three areas disposed concentrically, but it is apparent that the shading portion may be comprised of two or more areas disposed concentrically or may be comprised of a plurality of areas having other suitable shapes.

As described above, in the ophthalmic illumination apparatus of the present invention, the transmittance is electrically varied, whereby the degree of shading can be adjusted and therefore, for example, in an operation for a cataract, the fundus of an eye to be examined is protected from excessive illuminating light and also, comfortable operation becomes possible for the operator.

Further, no vibration is created by an electrical shading operation and therefore, even when for example, a microscope optical system is used, no vibration will result and the eye to be examined can be observed well.

What is claimed is:

1. An ophthalmic illumination apparatus for illuminating an eye to be examined with light, comprising:

a light source emitting illuminating light;

a shading device, including an electrical light control element having a transmittance that can be electrically varied, said shading device shading at least part of the illuminating light before the illuminating light illuminates said eye to be examined; and a controller that electrically varies the transmittance of said electrical light control element of the shading device.

2. The apparatus of claim 1, wherein said shading device is provided at a position substantially conjugate with the pupil of said eye to be examined.

3. The apparatus of claim 1, wherein said controller varies the transmittance of said electrical light control element of the shading device based on the intensity of the illuminating light emitted from said light source.

4. The apparatus of claim 3, wherein said controller reduces the transmittance of said electrical light control element of the shading device continuously or in a plurality of steps as intensity of the illuminating light emitted from said light source increases.

5. The apparatus of claim 1, wherein said shading device has a plurality of shading areas, in each of which an independently controlled electrical light control element is provided.

6. The apparatus of claim 5, wherein said controller can vary the transmittance of each of the shading areas of said shading device to thereby vary a shape or a distribution of brightness of the shading area.

7. The apparatus of claim 1, wherein said electrical light control element is an electrochromic element of the whole solid state type.

8. The apparatus of claim 1, wherein said controller varies the transmittance of said electrical light control element of the shading device continuously or in a plurality of steps.

* * * * *